United States Patent [19]

Dyckman

[11] Patent Number: 5,217,901
[45] Date of Patent: Jun. 8, 1993

[54] STERILIZATION BIOLOGICAL TEST PACK

[75] Inventor: John Dyckman, Mahopac, N.Y.

[73] Assignee: Propper Manufacturing Co., Inc., Long Island City, N.Y.

[21] Appl. No.: 803,718

[22] Filed: Dec. 5, 1991

Related U.S. Application Data

[63] Continuation of Ser. No. 460,825, Jan. 4, 1990, abandoned.

[51] Int. Cl.⁵ .................... C12M 1/34; C12Q 1/22
[52] U.S. Cl. .................... 435/291; 435/31; 435/287; 422/58; 422/61; 436/1
[58] Field of Search .............. 435/31, 287, 291; 422/58, 61; 436/1; 206/459, 807

[56] References Cited

U.S. PATENT DOCUMENTS

| | | | |
|---|---|---|---|
| 3,996,802 | 1/1976 | Smith | 422/119 |
| 4,486,387 | 12/1984 | Augurt | 422/58 |
| 4,576,795 | 3/1986 | Bruso | 422/58 |
| 4,579,715 | 4/1986 | Bruso | 422/58 |
| 4,596,696 | 6/1986 | Scoville, Jr. | 435/31 |
| 4,636,472 | 1/1987 | Bruso | |
| 4,692,307 | 9/1987 | Bruso | 422/58 |
| 4,699,765 | 10/1987 | Hambleton | 422/58 |
| 4,863,867 | 9/1989 | Joyce et al. | 435/287 |
| 4,902,478 | 2/1990 | Hambleton | 435/31 |
| 4,918,003 | 4/1990 | Macaro et al. | 435/31 |

Primary Examiner—James C. Housel
Assistant Examiner—Jan M. Ludlow
Attorney, Agent, or Firm—Amster, Rothstein & Ebenstein

[57] ABSTRACT

A sterilization biological test pack comprises a first plurality of apertured planar sheets of substantially porous paper disposed to form a stack. Each of the sheets defines a generally centrally disposed aperture, the apertures operatively defining together a single cavity extending through the stack. Second and third pluralities of unapertured planar sheets of substantially porous paper are disposed on opposed sides of the stack and aligned therewith to close the stack cavity at either end thereof and define a chamber about the cavity configured and dimensioned to receive a biological indicator. Fourth and fifth pluralities of unapertured planar sheets of paper of intermediate porosity are disposed on exposed sides of the third and fourth pluralities, respectively, and aligned therewith. A sheet of unapertured paper of a low but appreciable porosity is disposed as an overwrap all about the periphery of the assembly of the first, second, third, fourth and fifth pluralities to control passage of steam and air into and from the assembly, whereby the overwrapped assembly presents a challenge of graded decreasing porosity from the biological indicator in the chamber to both sides of the overwrapped assembly.

23 Claims, 3 Drawing Sheets

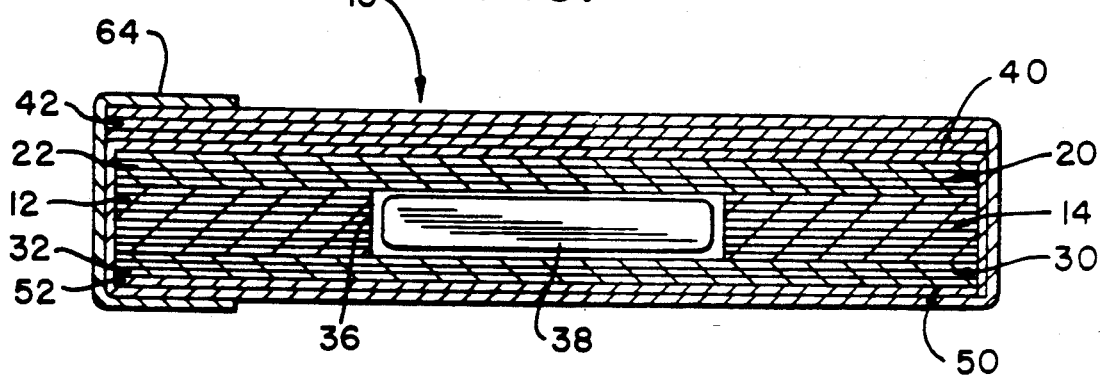
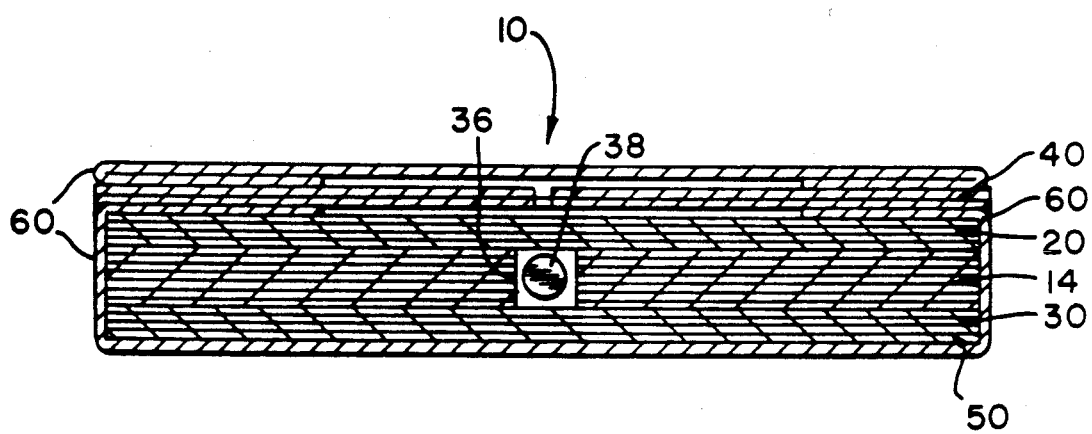

STERILIZATION BIOLOGICAL TEST PACK

This is a continuation of copending application Ser. No. 07/460,825, filed on Jan. 4, 1990, now abandoned.

BACKGROUND OF THE INVENTION

This invention relates generally to packs for testing the efficacy of a sterilization system. More specifically, the invention relates to a test pack which can be used with either a biological indicator or a chemical indicator to determine the efficacy of the sterilization system. The present invention is particularly, although not exclusively, useful for the testing of sterilizing equipment used for the sterilization of hospital and medical equipment.

The sterilization of medical equipment by exposure to steam is typically accomplished by using an autoclave. Normally, the equipment to be sterilized is placed within the autoclave and a vacuum may be drawn depending on the particular procedure being followed. The sterilization medium, steam, is then introduced into the autoclave to permeate the equipment and sterilize it.

According to standard hospital procedures, steam sterilization equipment needs to be periodically tested to insure the sterilization process is efficacious. Such a test preferably requires subjecting spores of living microorganisms to the sterilization cycle and subsequently observing whether they have remained viable. To insure that the sterilization process is efficacious by sufficiently challenging the sterilization equipment, these spores need to be protected as well or better than they would ordinarily be Protected if lodged in the most inaccessible recesses of the hospital packs to be sterilized.

Several procedures have been proposed to test the efficacy of steam sterilization equipment. Typical of these, and perhaps the best known and most widely used, is the procedure recently published by the Association for the Advancement of Medical Instrumentation (A.A.M.I.). According to the A.A.M.I. recommended practice, freshly laundered all-cotton towels are folded by hospital personnel and stacked to construct a test pack into which a biological indicator is imbedded. This pack is then subjected to the sterilization cycle.

Although apparently efficacious for its intended purpose, the construction of a test pack according to the A.A.M.I. procedure is labor intensive and the resulting pack is relatively bulky. In light of these limitations, the present invention satisfies the need for a pre-assembled composite sterilization test pack which is convenient to handle and which will sufficiently challenge steam sterilization equipment. This is accomplished by surrounding a biological indicator with material which will delay steam entry to the indicator and provide the indicator with a degree of thermal insulation.

U.S. Pat. No. 4,636,472 discloses such a pre-assembled composite sterilization test pack which employs a combination of porous and non-porous materials in order to effect the desired interplay of steam entry to the indicator and degree of thermal insulation. The patented disposable sterilization test pack includes a base pad comprising a plurality of porous sheets having holes cut therethrough which are stacked to align the holes and form a cavity for receiving a sterilization indicator therein. A top pad and a bottom pad, each of gas permeable porous material, are respectively placed against the top and bottom surfaces of the base pad to confine the indicator within the cavity and help inhibit the flow of gas to and from the cavity. A gas impermeable layer is disposed against the top pad on its surface which is opposite from the base pad to further inhibit gas flow to and from the cavity by preventing the passage of gas into and out of the test pack wherever the impermeable layer is in contact with the porous material of the top pad.

When subjected to a sterilization cycle, the sterilization indicator (e.g., a biological or chemical indicator), positioned in the cavity of the test pack's base pad, will react according to the efficacy of the sterilization cycle. The entire stack of layers can be covered with a CSR (central supply room) overwrap material and held together with a tape having an indicator ink imprinted thereon to show when a pack has been subjected to a sterilization process.

The patented test pack has not proven to be entirely satisfactory in use. The use of a gas impermeable layer substantially precludes gas flow to and from the cavity through a major surface (that is, the top) of the test pack and thereby emphasizes the flow of gas to and from the cavity along the edges and intermediate the pads (or intermediate the several sheets forming the pads) of the test pack. This is especially true in the preferred embodiments wherein there is also a gas impermeable layer disposed against the bottom pad. The resultant emphasis on gas flow along the edges of the test pack and intermediate the pads thereof makes the efficacy of the pack highly sensitive to the degree of tightness with which the overwrap material is applied thereto, by affecting the ability of the gas blocked by the gas impermeable layer to nonetheless reach the cavity by passage within the test pack intermediate the overwrap material and the sides of the stack and then intermediate the adjacent faces of the more permeable sheets of the stack. Furthermore, as the patented test pack utilizes a porous overwrap material, it is necessary to vary the number, size or composition of the basic stack (that is, the materials within the overwrap) in order to vary the challenge.

Accordingly, it is an object of the present invention to provide a pre-assembled sterilization test pack which tests the efficacy of steam sterilization biological equipment by challenging the accessibility of steam to the indicator and providing a requisite level of thermal insulation for the indicator.

Another object provides such a test pack which can be easily altered to change sterilization indicators according to the needs and desires of the operation.

Still another object is to provide such a pre-assembled test pack which is small, compact, easily handled by hospital personnel, convenient to use, standardized, cost effective and easily manufactured.

It is also an object of the present invention to provide such a test pack which does not use gas impermeable layers to preclude the passage of gas into and out of the test pack.

It is another object to provide such a test pack in which the challenge may be varied without modification of the basic assembly of layers within the overwrap paper.

SUMMARY OF THE INVENTION

It has now been found that the above and related objects of the present invention are obtained in a sterilization biological test pack comprising first, second, third, fourth and fifth pluralities of sheets of paper and an overwrap. The first plurality is formed of apertured planar sheets of substantially porous paper disposed to form a stack, each of the sheets defining a generally centrally disposed aperture, and the apertures of the sheets operatively defining together a single cavity extending through the stack. The second plurality is formed of unapertured planar sheets of substantially porous paper disposed to one side of the stack and aligned therewith. The third plurality is formed of unapertured planar sheets of substantially porous paper disposed to an opposed side of the stack and aligned therewith. The second and third pluralities of unapertured sheets extend across the stack cavity at either end thereof to close the same and define a chamber about the cavity configured and dimensioned to receive a biological indicator. The fourth plurality is formed of unapertured planar sheets of paper of intermediate porosity, the fourth plurality being disposed on an exposed side of the second plurality and aligned therewith. The fifth plurality is formed of unapertured planar sheets of paper of intermediate porosity, the fifth plurality being disposed on an exposed side of the third plurality and aligned therewith. A sheet of unapertured paper of a low but appreciable porosity is disposed as an overwrap all about the periphery of the assembly of the first, second, third, fourth and fifth pluralities to control passage of steam and air into and from the assembly. The overwrapped assembly presents a challenge of graded decreasing porosity from the chamber to both sides of the overwrapped assembly.

In a preferred embodiment, the sheets of the first, second, third, fourth and fifth pluralities forming the assembly are of identical peripheral dimensions, typically 5×5 to 5×5.5 inch sheets. The chamber is about 1⅞×½ to 2⅝×¾ inch in area.

The first plurality is preferably comprised of about 18 to about 24 sheets of paper having a basis weight of about 214 lbs., a caliper of about 0.02 in., and a Gurley porosity of about 12-35 sec. (20 oz. cylinder). More particularly, the first, second, third, fourth and fifth pluralities forming the assembly are either about 5×5 in. sheets, with the first plurality being formed of 18 sheets and the chamber being 1⅞×½ in. in area, or about 5×5.5 in sheets, with the first plurality being formed of 24 sheets and the chamber being 2⅝×¾ in. in area.

The second and third pluralities are preferably each comprised of about 13 sheets of paper. Optimally the sheets of substantially porous paper for the first, second and third pluralities are of the same composition.

The fourth and fifth pluralities are each comprised of about 2 sheets of paper having a basis weight of about 134 lbs., a caliper of about 0.0088 in., and a Gurley porosity of about 20 min. (20 oz. cylinder).

The overwrap sheet of low but appreciable porosity is paper having a basis weight of about 43 lbs. and a Gurley porosity of about 30-50 min. (20 oz. cylinder). The overwrap sheet is paper saturated with an elastomer latex and disposed in a hospital pack format about the assembly.

The present invention also encompasses the test pack and a biological indicator disposed in the chamber.

BRIEF DESCRIPTION OF THE DRAWING

The above brief description, as well as further objects and features of the present invention, will be more fully understood by reference to the following detailed description of the presently preferred, albeit illustrative embodiments of the present invention when taken in conjunction with the accompanying drawing wherein:

FIG. 4 is a sectional view thereof taken along the line 4—4 of FIG. 3; and

FIG. 5 is a sectional view thereof taken along the line 5—5 of FIG. 3.

DETAILED DESCRIPTION OF THE PREFERRED EMBODIMENTS

Figure 1:
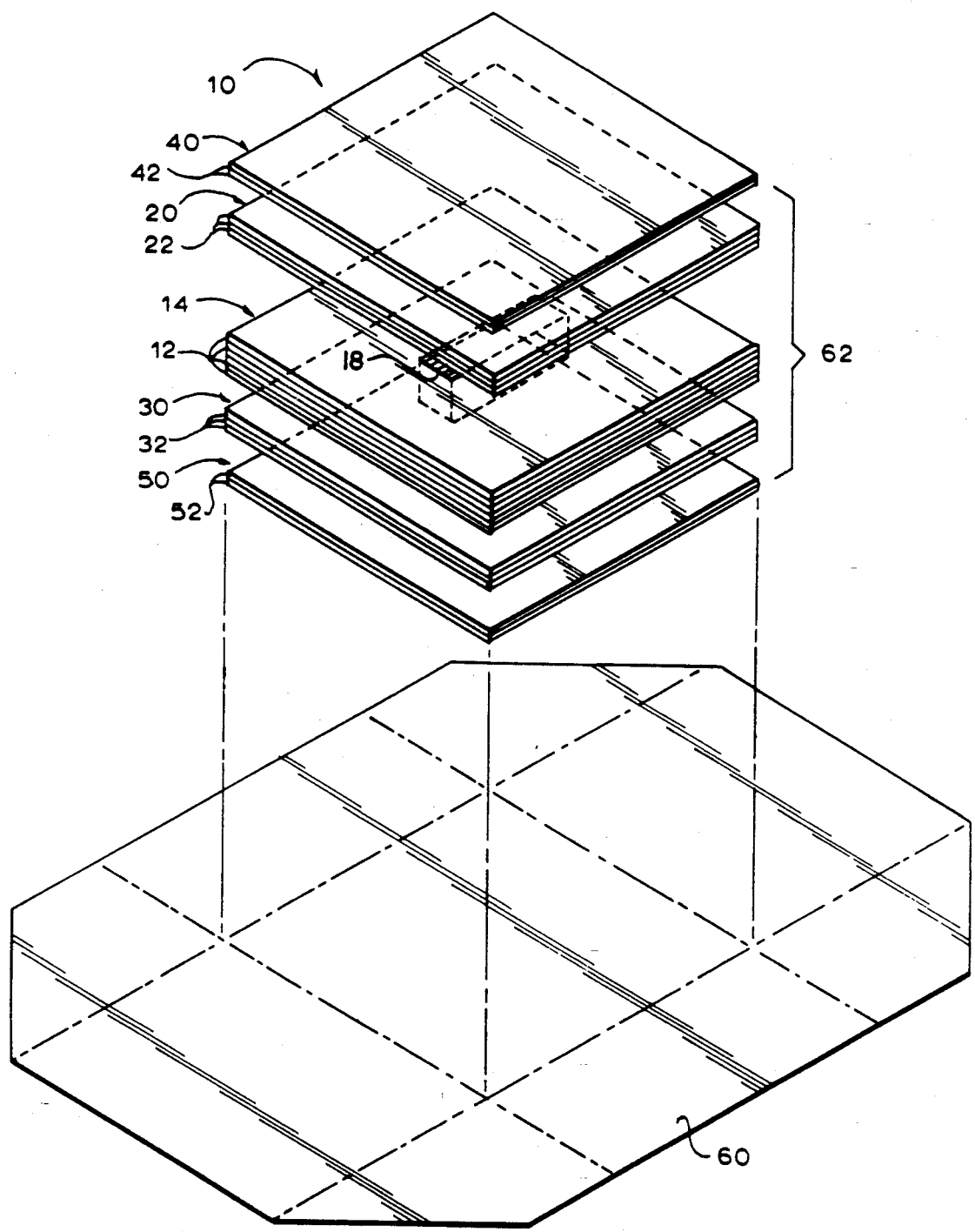
FIG. 1 is an exploded view of a test pack according to the present invention.
Figure 3:
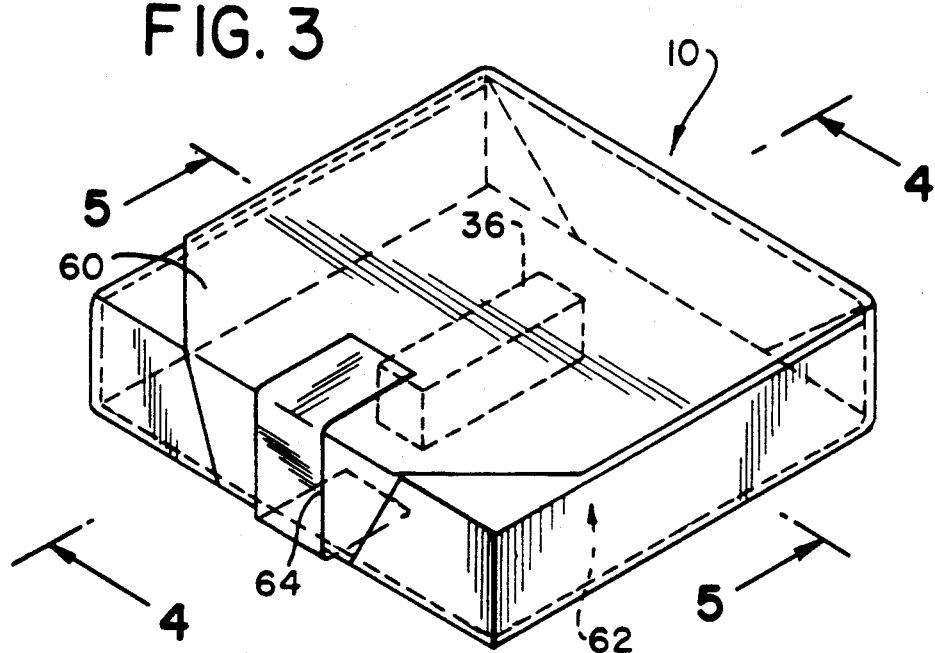
FIG. 3 is an isometric view of an assembled test pack.
Figure 2:
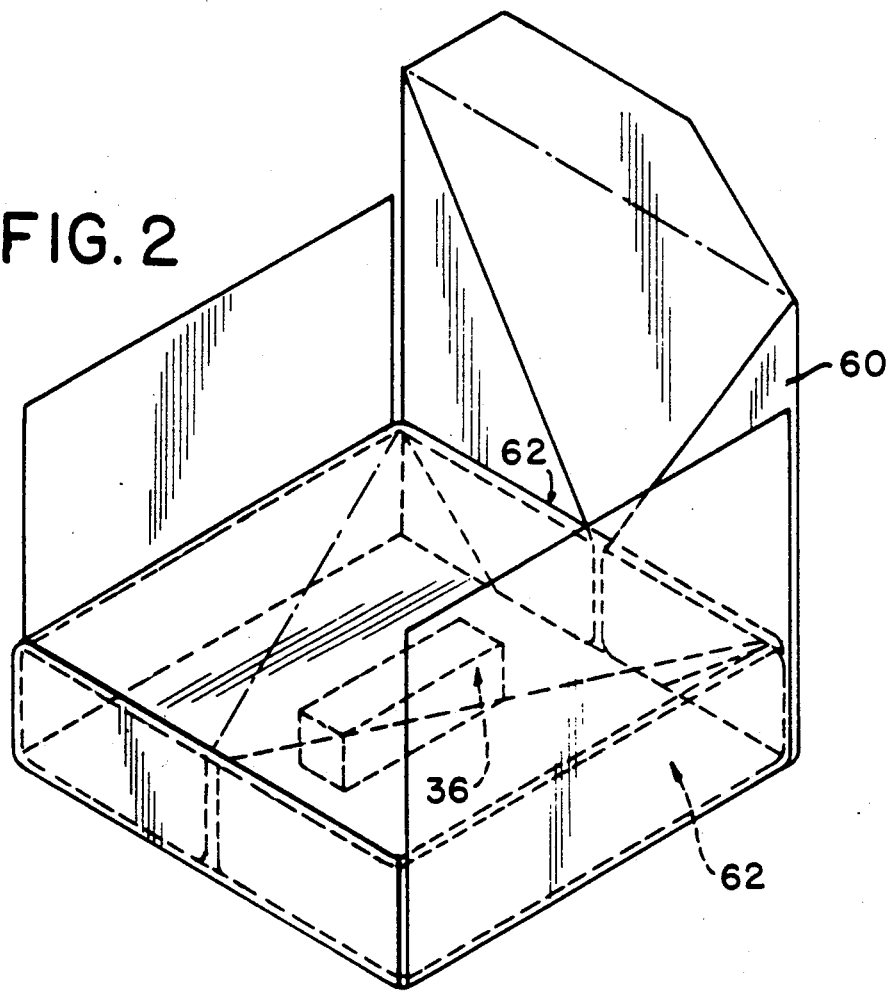
FIG. 2 is an isometric view of the basic stack in an intermediate stage of wrapping.

Referring now to the drawing, and in particular to FIGS. 3-5 thereof, therein illustrated is a sterilization biological test pack according to the present invention, generally designated by the reference numeral 10. As best seen in the exploded view of FIG. 1, the test pack 10 comprises a first plurality generally designated 14 of apertured planar sheets 12 of substantially porous paper disposed to form a stack. More particularly, the stack 14 is comprised of from about 18 to about 24 sheets of paper having a basis weight of about 214±25 lbs. (per 3,000 sq. ft.), a caliper or thickness of about 0.02±0.005 in., and a Gurley porosity of about 12-35 sec. (using a 20 oz. cylinder). (The Gurley porosity test consists of timing the flowing of 100 cc of air through 1 square inch of the paper being tested, and produces results comparable to those of ASTM D726-58 Method A.) Suitable paper is available from James River Corporation in Richmond, Va.

The sheets 12 are about 5×5 or 5×5.5 in. in area, although clearly smaller and larger sheets may be used. Each of the sheets 12 defines a generally centrally disposed aperture, the several apertures of the sheets 12 operatively defining together a single cavity 18 extending through the stack 14. The apertures are die cut, of rectangular configuration, about 1⅞×½ or 2⅝×¾ in. in area (depending on the size of the biological indicator to be used), and vertically aligned, although clearly apertures of different configurations and dimensions are also useful. Preferably 18 sheets of 5×5 in. paper with a 1⅞×½ in. aperture or 24 sheets of 5×5.5 in. paper with a 2⅝×¾ in. aperture are used. Depending upon the number of sheets 12 forming the stack 14, the height of the cavity 36 is about ⅜ in. for the 5×5 stack and about ½ in. for the 5×5.5 stack.

A second plurality generally designated 20 formed of unapertured planar sheets 22 of substantially porous paper is disposed to one side of the stack 14 (for example, the top thereof) and aligned therewith. A third plurality generally designated 30 of unapertured planar sheets 32 of substantially porous paper is disposed to an opposed side of the stack 14 (for example, the bottom thereof) and aligned therewith. The second and third pluralities 20, 30 of unapertured planar sheets 22, 32 are each preferably comprised of about 13 sheets of substantially porous paper. The paper sheets 22, 32 are the same in peripheral dimensions, and preferably composition also, as the paper sheets 12 used in the first plurality or stack 14.

The second and third pluralities 20, 30 of unapertured sheets 22, 32 extend across the stack cavity 18 at either end thereof (that is, at the top thereof and the bottom thereof) to close the cavity and define a chamber 36 (see FIG. 3) about the cavity 18 configured and dimensioned to receive a biological indicator 38 (see FIGS. 4 and 5).

As one and two component biological indicators of the type suitable for use in the sterilization biological test pack 10 are well known in the art, a further specification thereof is not deemed necessary herein. The biological indicator is, of course, configured and dimensioned to be received within the chamber 36.

A fourth plurality generally designated 40 of unapertured planar sheets 42 of paper of intermediate porosity is disposed on an exposed side of the second plurality 20 (i.e., on the top thereof) and aligned therewith. A fifth plurality generally designated 50 of unapertured planar sheets 52 of paper of intermediate porosity is disposed on an exposed side of the third plurality 30 (i.e., on the bottom thereof) and aligned therewith. The fourth and fifth pluralities 40, 50 are each preferably comprised of about 2 sheets of unlaminated paper having a basis weight of about 134 lbs., a caliper of about 0.0088±0.00055 in., and a Gurley porosity of about 20±5 min. (using a 20 oz. cylinder). The unlaminated paper (typically used as laminating stock) is available under the tradename LC-088-AA-C from the Riegel Division of James River Corporation in Milford, N.J. The peripheral dimensions of the sheets of the fourth and fifth pluralities 40, 50 correspond to those of the sheets of the first, second and third pluralities 14, 20, 30. The sheets 42, 52 are preferably of the same composition.

A single sheet 60 of unapertured paper of a low but appreciable porosity is disposed as an overwrap all about the periphery of the assembly generally designated 62 and formed by the first, second, third, fourth and fifth pluralities 14, 20, 30, 40, 50. The overwrap sheet 60 essentially controls passage of steam and air into and from the assembly 62. The overwrap sheet 60 is preferably paper having a basis weight of about 43 lbs. and a Gurley porosity of about 30-50 min. (20 oz. cylinder). The overwrap sheet is available under the tradename #67011 from Canadian Technical Tape of Montreal, Canada. It is formed from creped Kraft paper having a density of 47 gm/sq. meter and a Gurley porosity of 6-8 sec. (200 ml., 4 ply), which is then saturated with an elastomer latex to reduce its porosity and optionally backsized. After autoclaving (250° F. and 16 psi for 17 minutes or 272° F. and 28 psi for 1.5 minutes), the Gurley porosity of the overwrap sheet 60 drops to about 6-12 minutes. The overwrap sheet 60 is preferably configured as an elongated hexagon (length 22 in. and width 14 in. for a 5×5.5 assembly) or octagon and disposed in a conventional hospital wrap format about the assembly 62. The overwrap sheet 60 is fully and tightly wrapped around the assembly 62 so that the passage of steam and air into and from the assembly 62 is essentially directly through the overwrap sheet 60 rather than through fold openings or the like in the wrapping of the overwrap sheet 60.

A short strip of standard adhesive autoclave tape 64, holds the overwrap sheet 60 in the desired overwrapping orientation. The autoclave tape 64 typically has a porosity similar to that of the overwrap sheet 60. The overall height of the pack is about 1 in. for the 5×5 pack and about 1⅛ in. for the 5×5.5 pack.

It will be appreciated that the overwrap assembly presents a challenge of highly graded or graduated porosity decreasing from the chamber 36 to both sides (that is, the top and bottom) of the overwrap assembly via the substantial porosity (12-35 sec. Gurley) of the sheets 12, 22, 32 of the first, second and third pluralities 14, 20, 30, the intermediate porosity (20 min. Gurley) of the sheets 42, 52 of the fourth and fifth pluralities 40, 50, and finally the low but appreciable porosity (30-50 min. Gurley) of the overwrap sheet 60. Thus the entire test pack 10 is devoid of any nonporous (i.e., gas-impermeable) material so that there is always a component of the steam and air passing into and from the chamber 36 vertically through the sheets 22, 42, 60 or 32, 52, 60 as well as a component passing horizontally through overwrap sheet 60 and intermediate other sheets (for example, intermediate sheets 12), and various hybrid components which travel to some degree horizontally and/or vertically intermediate the overwrap sheet 60 and the periphery of the assembly 62. Thus, due to the existence of the several components, the test pack 10 of the present invention is less sensitive to the tightness with which the overwrap sheet 60 is applied to the assembly 62, and thus provides more reliable results regardless of who is to do the overwrapping or how tightly it is done on a given test pack.

The level of challenge provided by the test pack 10 according to the present invention may be varied, without changing the assembly 62, in a relatively predictable manner. This may be accomplished either by varying the porosity of the overwrap sheet 60 or by maintaining the porosity of the overwrap sheet 60 a constant but varying the size of the overwrap sheet 60 so as to enable the assembly 62 to be wrapped in a different number of layers or fractions of layers of the overwrap sheet 60. Thus the overwrap sheet 60 may be doubled, tripled or the like prior to application about the assembly 62, thereby to increase its effective thickness intermediate the chamber 36 and the sterilizing atmosphere outside of the test pack 10, and thereby correspondingly diminishing the effective porosity of the overwrapping so as to increase the challenge presented. Alternatively, rather than making multiple folds of the overwrap sheet 60 prior to its application to the assembly 62, a single layer of overwrap sheet 60 may be wrapped several times about the assembly 62, again so as to present multiple layers thereof to impede passage of steam and gas between the ambient atmosphere and the chamber 36. Thus, the challenge presented by the test pack 10 may be varied without any variation in the number, size or composition of the assembly 62 (that is, the overwrapped materials).

In use, the assembly 62 is built serially from the bottom to the top with a biological indicator 38 being placed within the cavity 18 of the stack 14 prior to closure of the chamber 36. The assembly 62 (now including the biological indicator 38) is then wrapped with overwrap sheet 60 as desired. Adhesive tape 64 is finally applied in order to hold the overwrap sheet 60 in place. Alternatively, the test pack may be sold preassembled with a biological indicator 38 in the chamber 36.

It will be appreciated that only representative sheets 12, 22, 32, 42, 52 of each plurality 14, 20, 30, 40, 50 are illustrated in the drawing.

To summarize, the present invention provides a test pack which is small, compact, easily handled by hospital personnel, convenient to use, standardized, cost effective and easily manufactured. It is easily altered to change sterilization indicators as desired, and the challenge may be varied without modification of the assembly within the overwrap paper. The test pack is devoid of any gas-impermeable layers which would preclude passage of steam and air into and out of the test pack.

Now that the preferred embodiments of the present invention have been shown and described in detail, various modifications and improvements thereon will become readily apparent to those skilled in the art. Accordingly, the appended claims are to b construed broadly and in a manner consistent with the spirit and scope of the invention described herein.

I claim:

1. A sterilization biological test pack enclosure for holding a biological indicator, comprising:
   (A) a first plurality of apertured planar sheets of paper having a first porosity disposed to form a stack, each of said sheets defining a generally centrally disposed aperture, and said apertures of said sheets operatively defining together a single cavity extending through said stack;
   (B) a second plurality of unapertured planar sheets of paper having a second porosity disposed to one end of said stack and aligned therewith
   (C) a third plurality of unapertured planar sheets of paper having a third porosity disposed to an opposed end of said stack and aligned therewith, said second and third pluralities of unapertured sheets extending across said stack cavity at either end thereof to close said stack cavity and define a chamber about said cavity configured and dimensioned to receive a biological indicator;
   (D) a fourth plurality of unapertured planar sheets of paper having a fourth porosity, said fourth plurality being disposed on an exposed end of said second plurality of unapertured sheets and aligned therewith;
   (E) a fifth plurality of unapertured planar sheets of paper having a fifth porosity, said fifth plurality being disposed on an exposed end of said third plurality of unapertured sheets and aligned therewith; and
   (F) a sheet of paper having a sixth porosity disposed as an overwrap all about the periphery of the assembly of said first, second, third, fourth and fifth pluralities of sheets to cover all of the side and end surfaces thereof with said overwrap, at least partially overlapping itself to form multiple layers covering substantially at least one entire surface of said assembly, to control passage of stream and air into and from said assembly; said first, second, and third porosities being greater than said fourth and fifth porosities which are in turn greater than said sixth porosity
   whereby said overwrapped assembly presents a challenge of graded decreasing porosity from said chamber to both ends of said overwrapped assembly and enables the challenge to be varied by varying the size of said overwrap sheet and thereby the overlap of said overwrap sheet upon itself.

2. In combination, the test pack of claim 1 and a biological indicator disposed in said chamber.

3. The test pack enclosure of claim 1 wherein said chamber is about $1\frac{7}{8} \times \frac{1}{2}$ to $2\frac{5}{8} \times \frac{3}{4}$ inch in area.

4. The test pack enclosure of claim 1 wherein said sheets of said fourth and fifth pluralities are of the same composition.

5. The test pack enclosure of claim 1 wherein said overwrap is disposed in a hospital pack format about said assembly.

6. The test pack enclosure of claim 1 wherein said overwrap sheet has sufficient porosity to affect the challenge presented by said test pack.

7. The test pack enclosure of claim 1 wherein said overwrap sheet is unapertured and characterized by a substantially uniformly distributed porosity.

8. The test pack enclosure of claim 1 wherein said sheets of said first, second, third, fourth and fifth pluralities forming said assembly are of identical peripheral dimensions.

9. The test pack enclosure of claim 8 wherein said sheets of said first, second, third, fourth and fifth pluralities forming said assembly are about $5 \times 5$ to $5 \times 5.5$ inch sheets.

10. The test pack enclosure of claim 1 wherein said sheets of said second and third pluralities are of the same composition.

11. The test pack enclosure of claim 10 wherein said sheets of said first, second and third pluralities are of the same composition.

12. The test pack enclosure of claim 1 wherein said first plurality is comprised of sheets of paper having a basis weight of about 214 lbs., a caliper of about 0.02 in., and a Gurley porosity of about 12-35 sec. (20 oz. cylinder).

13. The test pack enclosure of claim 12 wherein said first plurality is comprised of about 18 to 24 of sheets of said paper.

14. The test pack enclosure of claim 13 wherein said first, second, third, fourth and fifth pluralities forming said assembly are about $5 \times 5$ in. sheets, said first plurality is formed of 18 sheets, and said chamber is $1\frac{7}{8} \times \frac{1}{2}$ in. in area.

15. The test pack enclosure of claim 13 wherein said first, second, third, fourth and fifth pluralities forming said assembly are about $5 \times 5.5$ in sheets, said first plurality is formed of 24 sheets, and said chamber is $2\frac{5}{8} \times \frac{3}{4}$ in. in area.

16. The test pack enclosure of claim 13 wherein said second and third pluralities are each comprised of about 13 sheets of paper having a basis weight of about 214 lbs., a caliper of about 0.02 in., and a Gurley porosity of about 12-35 sec. (20 oz. cylinder).

17. The test pack enclosure of claim 16 wherein said fourth and fifth pluralities are each comprised of about 2 sheets of paper having a basis weight of about 134 lbs., a caliper of about 0.0088 in., and a Gurley porosity of about 20 min. (20 oz. cylinder).

18. The test pack enclosure of claim 16 wherein said overwrap sheet is paper having a basis weight of about 43 lbs. and a Gurley porosity of about 30-50 min. (20 oz. cylinder).

19. The test pack enclosure of claim 18 wherein said overwrap sheet is paper saturated with an elastomer latex.

20. A sterilization biological test pack enclosure for holding a biological indicator, comprising:
   (A) a first plurality of apertured planar sheets of paper having a first porosity disposed to form a stack, each of said sheets defining a generally centrally disposed aperture, and said apertures of said sheets operatively defining together a single cavity extending through said stack, said first plurality of sheets being comprised of about 18 to 24 sheets of paper having a basis weight of about 214 lbs., a caliper of about 0.02 in., and a Gurley porosity of about 12 to 35 sec. (20 oz. cylinder);
   (B) a second plurality of unapertured planar sheets of paper having a second porosity disposed to an opposed end of said stack and aligned therewith;

(C) a third plurality of unapertured planar sheets of paper having a third porosity disposed to an opposed end of said stack and aligned therewith, said second and third pluralities of unapertured sheets each being comprised of about 13 sheets of paper having a basis weight of about 214 lbs., a caliper of about 0.02 in., and a Gurley porosity of about 12 to 35 sec. (20 oz. cylinder), said second and third pluralities of unapertured sheets extending across said stack cavity at either end thereof to close said stack cavity and define a chamber about said cavity configured and dimensioned to receive a biological indicator;

(D) a fourth plurality of unapertured planar sheets of paper having a fourth porosity, said fourth plurality of unapertured sheets being disposed on an exposed end of said second plurality of unapertured sheets and aligned therewith;

(E) a fifth plurality of unapertured planar sheets of paper having a fifth porosity, said fifth plurality of unapertured sheets being disposed on an exposed end of said third plurality of unapertured sheets and aligned therewith, said fourth and fifth pluralities of unapertured sheets each being comprised of about 2 sheets of paper having a basis weight of about 134 lbs., a caliper of about 0.0088 in., and a Gurley porosity of about 20 min. (20 oz. cylinder);

(F) a sheet of paper having a sixth porosity disposed as an overwrap in a hospital pack format all about the periphery of the assembly of said first, second, third, fourth and fifth pluralities of sheets to cover all of the side and end surfaces thereof, with said overwrap sheet at least partially overlapping itself to form multiple layers covering substantially at least one entire surface of said assembly, to control passage of stream and air into and from said assembly, said overwrap sheet being paper saturated with an elastomeric latex and having a basis weight of about 43 lbs. and a Gurley porosity of about 30–50 min. (20 oz, cylinder); and (G) a biological indicator disposed in said chamber; said first, second, and third porosities being greater than said fourth and fifth porosities which are in turn greater than said sixth porosity whereby said overwrapped assembly presents a challenge of graded porosity decreasing from said chamber to both ends of said overwrapped assembly and enables the challenge to be varied by varying the size of said overwrap sheet and thereby the overlap of said overwrap sheet upon itself.

21. The test pack enclosure of claim 20 wherein said overwrap sheet has sufficient porosity to affect the challenge presented by said test pack.

22. The test pack of claim 20 wherein said overwrap sheet is unapertured and characterized by a substantially uniformly distributed porosity.

23. Kit for customized assembly of a sterilization biological test pack enclosure for holding a biological indicator, comprising:

(A) a first plurality of apertured planar sheets of paper having a first porosity disposed to form a stack, each of said sheets defining a generally centrally disposed aperture, and said apertures of said sheets operatively defining together a single cavity extending through said stack;

(B) a second plurality of unapertured planar sheets of paper having a second porosity disposed to one end of said stack and aligned therewith;

(C) a third plurality of unapertured planar sheets of paper having a third porosity disposed to an opposed end of said stack and aligned therewith, said second and third pluralities of unapertured sheets extending across said stack cavity at either end thereof to close said stack cavity and define a chamber about said cavity configured and dimensioned to receive a biological indicator;

(D) a fourth plurality of unapertured planar sheets of paper having a fourth porosity, said fourth plurality being disposed on an exposed end of said second plurality of unapertured sheets and aligned therewith;

(E) a fifth plurality of unapertured planar sheets of paper having a fourth porosity, said fifth plurality being disposed on an exposed end of said third plurality of unapertured sheets and aligned therewith; and (F) a sheet of paper having a sixth porosity configured and dimensioned to be disposed as an overwrap all about the periphery of the assembly of said first, second, third, fourth and fifth pluralities of sheets to cover all of the side and end surfaces thereof, thereby to control passage of steam and air into and from said assembly, said overwrap sheet being of sufficient size relative to said assembly to enable said overwrap sheet, when overwrapped about said assembly, to at least partially overlap itself to form multiple layers covering substantially at least one entire surface of said assembly; said first, second, and third porosities being greater than said fourth and fifth porosities which are in turn greater than said sixth porosity whereby said overwrapped assembly presents a challenge of graded decreasing porosity from said chamber to both ends of said overwrapped assembly and enables the challenge to be varied by varying the size of said overwrap sheet and thereby the overlap of said overwrap sheet upon itself.

* * * * *